(12) United States Patent
Lamb

(10) Patent No.: US 9,901,626 B2
(45) Date of Patent: Feb. 27, 2018

(54) METHOD OF TREATING FIBROSIS IN SKELETAL MUSCLE TISSUE

(71) Applicant: G. Blair Lamb, Kilbride (CA)

(72) Inventor: G. Blair Lamb, Kilbride (CA)

( * ) Notice: Subject to any disclaimer, the term of this patent is extended or adjusted under 35 U.S.C. 154(b) by 0 days.

(21) Appl. No.: 14/763,367

(22) Filed: Jul. 24, 2015

(65) Prior Publication Data

US 2015/0359860 A1    Dec. 17, 2015

Related U.S. Application Data

(63) Continuation-in-part of application No. PCT/CA2014/000052, filed on Jan. 28, 2014, which is a continuation of application No. 13/751,673, filed on Jan. 28, 2013, now abandoned.

(51) Int. Cl.
| | |
|---|---|
| *A61K 38/48* | (2006.01) |
| *A23K 1/165* | (2006.01) |
| *A61K 38/46* | (2006.01) |
| *A23K 20/189* | (2016.01) |

(52) U.S. Cl.
CPC ........ *A61K 38/4886* (2013.01); *A23K 20/189* (2016.05); *A61K 38/465* (2013.01); *A61K 38/482* (2013.01); *A61K 38/4873* (2013.01); *C12Y 304/21062* (2013.01); *C12Y 304/2404* (2013.01); *C12Y 304/21031* (2013.01); *C12Y 304/22002* (2013.01)

(58) Field of Classification Search
None
See application file for complete search history.

(56) References Cited

U.S. PATENT DOCUMENTS

| | | | |
|---|---|---|---|
| 4,039,658 | A | 8/1977 | King |
| 4,055,635 | A | 10/1977 | Green et al. |
| 6,440,414 | B1 | 8/2002 | Kendrick et al. |
| 2003/0129218 | A1 | 7/2003 | Smoler et al. |
| 2007/0116699 | A1* | 5/2007 | Holsworth ......... A61K 38/4886 424/94.63 |
| 2008/0317774 | A1* | 12/2008 | Sakaguchi ............ A61K 36/03 424/195.17 |
| 2010/0135919 | A1 | 6/2010 | Barron |

FOREIGN PATENT DOCUMENTS

| | | |
|---|---|---|
| JP | 2009 185058 | 8/2009 |
| WO | 2008/019417 | 2/2008 |
| WO | 2008/021987 | 2/2008 |

OTHER PUBLICATIONS

ImaRx Therapeutics, Inc., Kinlytic™ (urokinase for injection), Jun. 2007, Available Online at: dailymed.nlm.nih.gov/dailymed/fda/fdaDrugXsl.cfm?setid=bfe5cfb9-591d-4df8-12a3-6555cde3185d&type=display.*

Benjamin, Misperceived Headache Pain, Massage Today, Apr. 2008, vol. 08, Issue 04, Available Online at: www.massagetoday.com/mpacms/mt/article.php?id=13789.*
Mayo Clinic, Headache, Accessed Jul. 6, 2017, Available Online at: www.mayoclinic.org/symptoms/headache/basics/causes/sym-20050800.*
Al-Khateeb et al.: "Effect of the proteolytic enzyme serrapeptase on swelling, pain and trismus after surgical extraction of mandibular third molars", International Journal of Oral and Maxillofacial Surgery, Copenhagen, DK, vol. 37, No. 3, Feb. 12, 2008 (Feb. 12, 2008), pp. 264-268, XP022531810, ISSN: 0901-5027, DOI:10.1016/J.IJOM.2007.11.011 p. 265, col. 1, paragraph 4—p. 265, col. 3, paragraph 1.
Database WPI Week 200712 Thomson Scientific, London, GB: AN 2007-116714, XP002760061, & KR 100 581 076 B1 (Maniker Co Ltd) May 16, 2006 (May 16, 2006)—Abstract.
Fujiwara et al., Effect of Fermented Soybean, "Natto" on the Production and Qualities of Chicken Meat, Asian-Aust. J. Anim. Sci., vol. 21, No. 12 (Dec. 2008) 1766-1772.
Lluis, F. et al., "Urokinase-dependent plasminogen activation is required for efficient skeletal muscle regeneration in vivo", Blood, Mar. 15, 2001 (Mar. 15, 2001), vol. 97, No. 6, pp. 1703-1711, ISSN: 0006-4971. (whole document).
Suelves, M. et al., "Plasamin activity is required for myogenesis in vitro and skeletal muscle regeneration in vivo", Blood, Apr. 15, 2002 (Apr. 15, 2002), vol. 99, No. 8, pp. 2835-2844, ISSN: 0006-4971. (whole document).
Gunther, A. et al., "Prevention of Bleomycin-induced lung fibrosis by aerosolization of heparin or urokinase in rabbits", American Journal of Respiratory and Critical Care Medicine, (2003), vol. 168, pp. 1358-1365, ISSN: 1073-449X (whole document).
Tao of Herbs, Enzymes for Fibrin Control, Accessed online at: www.taoofherbs.com/articles/88/NeprinolEnzyme.htm, Available Oct. 16, 2007 (date information accessed from Internet Archive Wayback Machine) (serrapeptase and nattokinase break down fibrin deposits in injured tissue, including muscle, thereby reducing inflammation and pain).
Wikipedia, Fibrinolysis, Accessed Mar. 28, 2014, online at: en.wikipedia.org/wiki/Fibrinolysis (Fibrinolysis is a process which naturally occurs in the body; fibrin clots are broken down by the naturally occurring enzyme plasmin).
Wikipedia, Serratiopeptidase, Accessed Mar. 28, 2014, online at: en.wikipedia.org/wik/Serratiopeptidase (Serrapeptase is an enzyme produced by microorganisms in the intestines of silk worms).
Wikipedia, Nattokinase, Accessed Mar. 28, 2014, online at: en.wikipedia.org/wiki/Nattokinase (Nattokinase is an enzyme produced by microorganisms which ferment soybeans, producing natto, a food product well know in Japan).
Kuramoto, E. et al., "Inhalation of urokinase-type plasminogen activator reduces airways remodeling in a murine asthma model", American Journal of Physiology: Lung Cellular and Molecular Physiology, (2009), vol. 296, pp. L337-L346, ISSN: 1040-0605. (whole document).
AST Enzymes (Serracor-NK, Product Information, accessed online at: www.astenzymes.com/serracor-nk, available Jan. 11, 2011.

* cited by examiner

*Primary Examiner* — Karen Cochrane Carlson
*Assistant Examiner* — Jennifer M. H. Tichy
(74) *Attorney, Agent, or Firm* — Gowling WLG (Canada) LLP

(57) ABSTRACT

A method is disclosed to dissolve protein deposited in muscle. The method includes the step of administering an effective amount of an agent selected from the group consisting of fibrinolytics, proteolytics, photolytic and magnelytic agents.

9 Claims, No Drawings

METHOD OF TREATING FIBROSIS IN SKELETAL MUSCLE TISSUE

BACKGROUND

The present invention relates to the fields of chemistry and physiology, particularly protein chemistry and more particularly lipolytic, proteolytic and fibrinolytic compounds.

Fibrin is the basic building block of scar tissue that builds in the human or animal body. Although other proteins play a similar role in the body, fibrin is the major unit of scar deposition.

Some of the most studied areas where fibrin and other proteins have been shown to be deposited is in the blood vessels of the body, particularly the arteries. For example, U.S. Pat. No. 4,039,658 describes a new fibrinolytic enzymatic product having also anticoagulant properties is recovered from bile. It can be further purified to yield several fractions, all having similar activities, their molecular weights varying between about 5,000 and 50,000. The product or its fibrinolytically active derivatives are used to dissolve fibrin and inhibit blood coagulation in vivo or in vitro.

U.S. Pat. No. 4,055,635 describes a fibrinolytic pharmaceutical composition in unit dosage form suitable for administration by injection to humans which comprises an amount of a water soluble complex of a proteolytic enzyme sufficient to achieve the desired degree of fibrinolysis on administration to a human and linked covalently to a water-soluble polymeric substance having a molecular weight of from 10,000 to 500,000. The enzyme and the polymeric substance are present in the ratio of 1:2 to 1:50 and the composition is substantially free of unreacted enzyme.

U.S. Pat. No. 6,440,414 discloses a pharmaceutical composition comprising a metalloproteinase fibrinolytic agent, a zinc stabilizer and, optionally, a bulking agent, in a pharmaceutically-acceptable buffer. This metalloproteinase fibrinolytic agent comprises a specific amino acid sequence.

SUMMARY

In one aspect of the invention a method to dissolve protein deposited in muscle is provided. The method comprises administering an effective amount of an agent selected from the group consisting of fibrinolytics, proteolytics, photolytic and magnelytic agents.

In a preferred embodiment, the muscle is skeletal muscles of the spine and/or limbs to alleviate pain.

In another preferred embodiment, the agent is fibrinolytic.

In another preferred embodiment, the agent is proteolytic.

In another preferred embodiment, the agent is a photolytic agent.

In another preferred embodiment, the agent is a magnelytic agent.

In a further preferred embodiment, the agent is administered topically, intravenously, intrathecally, orally, or mucosally.

In another preferred embodiment, the agent is administered via a rectal suppository, a nasal spray, optic drops, topical formulation, a vaginal composition or an intravenous composition.

In another preferred embodiment, the agent is administered via a rectal suppository.

In another preferred embodiment, the agent is administered via a nasal spray.

In another preferred embodiment, the agent is administered via optic drops. In another preferred embodiment, the agent is administered via a vaginal composition.

In another preferred embodiment, the agent is administered via an intravenous composition.

In another preferred embodiment, fibrinolytic is administered at a concentration in the range of about 0.1 to about 2 mg/ml in a physiologically acceptable solution.

In another preferred embodiment, the fibrinolytic agent is Serrapeptase and/or Nattokinase.

In another preferred embodiment, the fibrinolytic agent, such as Serrapeptase or Nattokinase, is administered orally in an amount of about 5000 IU (international units) in the form of one to four tablets three times daily.

In yet another embodiment, the agent is formulated to comprise, per 30 mls., 10-50,000 IU of each of Serrapeptase, Nattokinase, a lipase, Rutin, and/or amla, and optionally comprising other proteases and/or fibrinolytics.

In another preferred embodiment, the agent is formulated for mucosal or vaginal or rectal administration wherein the agent comprises a solution having the components mixed in a sterile solution of water producing a concentration of about 0.1% to 5%. A stronger or weaker solution may be used to reduce or enhance effects and other mixing agents may be used to enhance absorption transdermally such as DMSO.

In another preferred embodiment, the agent is formulated for pulmonary and nasal administration wherein the agent is delivered by a lung and nasal vaporizer inhaler (respectively) in a metered dosing mechanism.

In another preferred embodiment, an inhaler is provided that comprises 10-50,000 IU of Serrapeptase, Nattokinase, a lipase, Rutin, and/or amla, and optionally comprising other proteases and/or fibrinolytics. The fibrinolytics may be combined or used individually.

In another aspect a method is provided to treat consumable animal meat by administering to livestock a fibrinolytic agent to dissolve protein deposited in skeletal muscles, organs or tissues of farm animals to improve quality of farm animal products, i.e. to tenderize meat. In this regard, an animal feed product is provided comprising a fibrinolytic agent selected from the group consisting of serrapeptase, nattokinase, and combinations thereof combined with animal feed such as grain, sileage, roughage, and the like.

DETAILED DESCRIPTION

The present invention is founded on the concept that, in certain situations, fibrin and/or protein deposits may actually impair the healing process. In the case of skeletal muscles or smooth muscles, the fibrin deposition process is complicated. Any injury to the muscle, including direct trauma, repetitive activity or exercise, may trigger a shortening of the muscle that may then cause the deposition of fibrin and/or other proteins into key areas or shortened areas of the muscle causing scar formation, trigger point formation, and difficulty with re-elongation of the muscle to its normal or maximal length. This may cause sustained or prolonged shortening of skeletal muscle. Any muscle in the body may be affected in this way including those of the spine, limbs, smooth muscle, sensory organs, other organs, the head and face. This sustained shortening of muscle can contribute to a variety of different pathologies. These pathologies may initiate a chain of events that may then cause other conditions, which could be related to chronic pain and/or disease.

As a simple illustration, a person may lift a heavy rock and injure the hamstring muscle in one of their legs. Over the course of a few days, the injury often triggers shortening of the hamstring in the area of significant injury. This may then lead to the deposition of fibrin and other proteins into the muscle causing the formation of a scar. This prevents the return of the muscle to its previous length, but also effects normal functionality of shortening and elongation of the muscle to create power. Further, the area where the fibrin has been deposited may contribute to wasting, trigger point encapsulation, excessive muscle shortening, and chronic tendon elongation with traction, injury or strain. As a result, the muscle may become weaker in these areas. This sustained shortening may cause persistent pulling on the origin or insertion of a muscle, leading to partial or complete tearing of the tendon. The fibrin deposited in the muscle may form an area of the muscle staying contracted or shortened. Inside the contracture will often be excess current or electrical potential. These areas or points of abnormal electrical potential (excessive) are often medically named as trigger points. These trigger points can become quite rigid and resistant to therapy by stretching or other exercise. If several of these trigger points or large section of fibrin are deposited in the same muscle, gross weakness and dysfunction may occur in the muscle. A hamstring injury leading to this shortening and scarring process may occur from one single injury or repeated small injuries causing an accumulation of small injuries into one compounded injury. The result is similar; deposition of fibrin and other proteins into the shortened, injured muscle/tendon structure causing encapsulated excessive electrical activity, less functionality of the muscle, chronic shortening of the tendon, tendon inflammation, muscle weakness with risk of tear or strain.

Once muscles shorten then a set of other complications may occur. The shortened muscle can cause chronic traction to its tendon causing tendonitis, and even premature rupture. It may cause compression or mal-tracking of the joints above or below the origin and insertion leading to premature joint wear, cartilage wear, arthritis, joint pain, and swelling. It may cause muscle weakness, pain and referred pain from the trigger point to other body areas as the stretch of the trigger point from the attempted elongation of the muscle signals referred pain. This is unique in trigger point description and understanding. One example is that of the gluteus medius trigger points, which refer to the sole of the foot, causing plantar fasciitis. One would suspect a foot origin, when in fact the gluteus medius refers to the sole of the foot. A scar within the gluteus medius sustains elongation with walking which triggers a referral of pain perceived into the foot causing an apparent foot pain. The origin of the actual pain, however, is in the gluteus medius where treatment should be directed.

In the spine, which includes the cervical, thoracic spine, and the lumbosacral spine, the problem can be more complex. A typical example of spinal scar formation occurs when the muscles of the spine are injured by either single injury, repeated injury or over years of daily living. The muscles respond following the same pattern with shortening and eventual scarring from the laying down of fibrin/proteins. The main difference in the spinal muscles is that the deepest muscle layers (often known as the intrinsic spinal muscles-multifidus, rotator brevis and longus for example) can form "super-scars" or super-contractures. This is where most of the muscle becomes a solid scar where by fibrin and/or other proteins have been deposited to such a degree that the muscle functions poorly or not at all. Beyond this, there is significant shortening with impact on the other spinal elements around or near the deep spinal muscles affecting many other connected functions of the body.

The spinal elements include the spinal vertebrae, the spinal discs, the spinal cord, the spinal nerve roots, spinal ligaments, the spinal articulating joints (including the cartilage) as well as the deep and superficial muscles of the spine. These intrinsic spinal muscles (often known as the multifidus and the deep rotators, but also including other deep spinal muscles not mentioned) can become completely encapsulated in a scar or scars made up of fibrin and other proteins. Once these super contractures form on/in the deep muscles, they can cause compression of the spinal discs that can then lead to disk degeneration, bulging, herniation, and/or sequestration leading to other spinal disease or effects. The consequences of these disk injuries can then lead to spinal cord and spinal nerve root compression, injury or even paralysis. The spinal neuropathies can then lead to pain conditions or other diseases that can then cause further pain or diseases distally.

The superficial layer of spinal muscle may also form scar tissue that can contribute to compression or mal-position of vertebrae or other spinal elements leading to conditions such as scoliosis, disk compression, facet joint compression, spinal cord compression or irritation, nerve root compression or irritation and then go on to cause local or distal pathology or pain.

The next component in understanding the injury mechanism is that of "Cannon's Law" where tissues that are deprived of their sensory or motor component become supersensitive. In Cannon's Law, a spinal nerve that is compromised may cause electrical abnormalities down an arm or leg, which may then lead to significant and or temporary or permanent changes in the arm or leg. This is typically the result of altered nerve signal to the tissue causing a change in electrical behavior of the muscle or tissue.

In the case of skeletal muscle, where motor nerve impingement may be impaired, the muscles in the body may persistently shorten due to the lack of motor nerve signal that is normally transmitted to the muscle. A common case example is that of tennis elbow where the fourth, fifth or sixth motor nerve root may be impaired or compromised by a bulging disc in the neck (caused by shortened and/or scarred deep spinal muscles). This results in the forearm muscle shortening causing excessive and/or persistent muscle workload. That in turn causes inflammation and injury leading to the deposition of fibrin and or other proteins into the forearm muscle. The muscle shortening followed by the deposit of fibrin/proteins in the forearm extensors may then cause "trigger point" formation in the extensors of the forearm. This may then cause a traction injury to the tendon of the extensor causing tendinitis of the forearm extensor. This muscle shortening in the forearm extensor may also compress the elbow joint or cause abnormal tracking of the elbow joint leading to pain, crepitus and even degeneration of the elbow joint. It may also cause a similar compression syndrome in the wrist causing crepitus, pain or premature degeneration of the wrist joints.

The present invention comprises the use of enzymes and/or other chemicals, and/or light therapy and/or magnetic therapy to dissolve fibrin and/or other proteins deposited in muscle of the spine and limbs to result in benefits that are derived directly or indirectly from the dissolution of these proteins in the spine and/or limbs or elsewhere.

In one embodiment, proteolytic agents are utilized in the present method. Examples of proteolytic agents useful in the present method include, but are not limited to, serine proteases, threonine proteases, cysteine proteases, aspartate proteases, glutamic proteases and metalloproteases. Proteolytic agents may be used in the present method alone or in combination with one or more proteolytic agents.

In another embodiment, the present method may employ fibrinolytic enzymes. As used herein, the term "fibrinolytic" refers to any natural or synthetic substance, any recombinant protein, and any fragment, natural or synthesized, that has fibrinolytic activity, i.e. activity by which fibrin (a fibrous, non-globular protein involved in the clotting of blood) is degraded. Examples of fibrinolytic agents include, but are not limited to, streptokinase, tenecteplase, urokinase, reteplase, TPA-tissue plasminogen activator, anistraplase, plasmin, plasminogen, alteplase, chimeric plasminogen, plasminogen activator from animal or bacterial sources (vampire bate, staphlokinase), pro-urokinase, anisoylated complex with plasminogen, urokinase type plasminogen activator, Serrapeptase, Nattokinase, and fibrinolytic fragments thereof. Fibrinolytic agents may be used in the present method alone or in combination with one or more fibrinolytic agents or proteolytic agents.

A fibrinolytic and/proteolytic agent may optionally be combined with at least one pharmaceutically acceptable carrier or adjuvant. The expression "pharmaceutically acceptable" means acceptable for use in the pharmaceutical and veterinary arts, i.e. not being unacceptably toxic or otherwise unsuitable. Examples of pharmaceutically acceptable adjuvants are those used conventionally with a particular type of compound, and may include diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule or suspension are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, tableting agents, colouring agents and flavouring agents may also be present. Creams, lotions and ointments may be prepared for topical application using an appropriate base such as a triglyceride base. Such creams, lotions and ointments may also contain a surface active agent. Aerosol formulations, for example, for nasal delivery, may also be prepared in which suitable propellant adjuvants are used. Other adjuvants may also be added to the composition regardless of how it is to be administered, for example, preservatives, anti-oxidants, stabilizers, anti-microbial agents and the like may be added to the composition to optimize shelf-life.

The fibrinolytic and/or proteolytic agents may additionally be combined with one or more components that facilitate the activity of the fibrinolytic or proteolytic agent, or facilitates use of these agents in a particular treatment regimen. Examples of such additional components include other enzymes, e.g. serine proteases such as urokinase, papain and bromelain; enzyme co-factors, e.g. coenzyme Q or ubiquinone; anti-inflammatory agents, e.g. Rutin; and the like.

Thus, fibrinolytic and/or proteolytic agents may be administered topically, intravenously, by infusion, orally, rectally, intrathecally, by inhalation or sprayed through the nasal or lung passages, through the urethra into bladder, via ocular eye drops, via otic drops, topical drops, transcutaneous spray, through the vagina into uterus/vagina or injected directly into the tissues for local affect, which could be muscular, or into sites where scars exist. In addition, fibrinolytic therapies may be applied to the chest cavity, abdominal cavity, or cranium for affects on organs or brain tissue.

In accordance with the invention, a therapeutically effective amount of a selected fibrinolytic or proteolytic agent is administered to muscle in the present treatment method. As used herein, the term "mammal" is meant to encompass, without limitation, humans, domestic animals such as dogs, cats, horses, cattle, swine, sheep, goats and the like, as well as wild animals. The term "therapeutically effective amount" is an amount of the selected fibrinolytic or proteolytic agent indicated for treatment of a given condition while not exceeding an amount which may cause significant adverse effects. Suitable dosages of the selected agent will vary with many factors including the particular condition to be treated and the individual being treated. Appropriate dosages are expected to be in the range of about 5000 to 5 million IU (International Units or "units"), for example, from about 250,000 to 1.5 million IU, or from 5000 to 50,000 IU. Solutions may comprise a fibrinolytic or proteolytic agent in the range of about 0.1 to about 2 mg/ml in a physiologically acceptable solution, or about 0.1% to 5% w/v.

In another aspect of the invention, light having photolytic effects is applied, either alone or in combination with fibrinolytic and/or proteolytic agents, to treat scarred areas and various conditions as set out above. Photolytic treatment involves the application of light ranging from about 300 nm to 1500 nm at a target site. One or more halogen lights may be utilized to deliver photolytic therapy to a small area or a large area, depending on the size/depth of the area to be treated by the light. Halogen lights may deliver light having a frequency in the range of about 200 nm to about 6000 nm; however, by filtering the light through a water barrier, light at a frequency within the desired range of 300 nm to 1500 nm is delivered. The power range of a halogen light may vary from 5 Watts to 500 Watts. Approximately 40 to 80% of the generated power may be filtered utilizing the water. Therefore, a 100 W bulb would deliver a filtered light spectrum of 300 nm to 1500 nm with approximately 6000 to 20,000 mW of power. More bulbs or higher power bulbs may be utilized to increase the power of the light delivered in order to target a larger treatment area. In one embodiment, light having a wavelength in a range between 600 and 700 nm may be used and may exhibit a greater photolytic effect. Single frequencies or combined frequencies may be utilized.

Thus, a photolytic device comprising a single light source of 100 W in combination with water filtration may be used to treat a small area such as 4"×4" for a period of 5 to 10 minutes to create lysis of scar tissue and deliver a fibrinolytic and/or proteolytic affect to the tissue area. A larger device using nine 100 W halogen lights may be used to treat areas such as 12"×12". In another embodiment, a photolytic device the size of a tanning bed (e.g. 3'×8') may be used in the present method. The light source is situated below the bed, and may include 40 to 200 halogen lights of 100 W each. A large liquid or water filter bed lies between the lights and a glass support on which a patient or organic material to be treated sit.

Using the table size device, an individual lies on the table for a treatment interval of about 1 to 60 minutes per day, e.g. about 15 minutes, utilizing 8,000,000 mW of halogen light (80×100 watts) which is filtered using a liquid such as water, to achieve delivery of photolytic light ranging from 400 nm to 1500 nm. The smaller wavelengths of light such as 400 nm, penetrate to a depth of half an inch or less into the organic tissue. The larger wavelengths penetrate deeper and ultimately the longest wavelengths of 1400 to 1500 nm penetrate to a depth of up to about 18 inches. Thus, the use of combined light frequencies of 400 to 1500 nm covers all depths of the tissue being treated.

Application of photolytic light therapy facilitates the dissolution of fibrin and other protein in the muscles or tissues of the body or mammal being treated. This results in the dissolution of trigger points in muscles, for example, facilitating improved performance in the muscle and reduction of pain and injury. Fibrin and/or undesirable build-up of protein in the other tissues of the body such as renal tissue, adrenal tissue, brain tissue, connective tissue, and joints may also be treated in this manner. This dissolution of fibrin and proteins facilitates recovery from injury and disease processes that cause protein deposition in tissue. Concussions of the brain often are left with scar tissue made of fibrin and other proteins. Thus, photolytic light therapy may be used to dissolve the scar tissue in the brain and allow for improved recovery of concussion and brain injuries.

Full body photolytic therapy for one minute to 60 minutes per day, which may be broken down into one or more treatments for the purpose of treating medication withdrawal and facilitation of medication reduction, e.g. to narcotic medications. Benefits full body photolytic therapy lie in the combination of full spectrum and total body delivery of the light therapy which allows for reversal of symptoms of body pain, muscle spasm, excessive sweating and drug cravings typically seen in individuals attempting to reduce or withdraw off a narcotic substance.

Similar photolytic treatment within the range of 400 to 1500 nm may be utilized to treat farm animals to reduce the amount of scarring in the meat and improve the quality of the meat. This treatment may be used before the killing of the animal for at least about 1 month, preferably 2-3 months or more, or to treat meat after butchering. Typically the white light full-spectrum is used; However, selected frequencies of 600-800 nm may be more specific for meat-tenderization.

The present method is useful to treat ailments caused by or worsened by undesirable fibrin and/or protein deposits within the body. For example, the ingestion of fibrinolytics to dissolve fibrin that has deposited in a neck may help to treat neck pain. However, beyond the neck pain dissolving the fibrin in the neck may also help to dissolve the scar tissue that compresses the disks in the neck, allowing for recovery of disk disease and the referred pain related to the disc disease, such as the nerve root impingement in the neck, leading to arm pain and other conditions. Disease processes related to neuropathy caused by this process are also part of the invention.

Therefore, the dissolution of fibrin and other proteins (deposited in the form of scar tissue eventually leading to spinal compression and then to other conditions that could be in the nature of pain and/or disease) could be treated or reversed by this process.

The ingestion of fibrinolytics/proteolytics for the purpose of remodeling of fibrin and/or the other proteins in the musculoskeletal/smooth muscle system may have direct benefits or indirect benefits or both. Further, the use of fibrinolytics/proteolytics for purpose of remodeling of the fibrin/protein deposition in the organs, brain, may also have direct or indirect benefits in disease, illness or injury.

The present invention can be used to provide many different types of benefits to animals, including humans, in need of such therapy. For example, the methods and compositions can be used to dissolve, lyse, cut, remove, and/or mobilize scar tissue (fibrin/protein deposits) on the spine or limb muscles that cause shortening and reduced movement of muscle. Shortened muscles compress joints causing persistent or recurrent joint compression leading to premature joint wear, cartilage wear and eventually osteo-arthritis treatment. The invention can also be used to treat spinal joint compression leading to spinal joint compression, disk compression, disk wear, disk herniation, disk sequestration, spinal stenosis, spinal nerve and spinal cord compression or irritation from disk, bone entrapment caused by shortened muscles with scar, and the complications of the spinal cord and/or nerve root compression and/or irritation such as vertigo, tinnitus, headaches, TMJ or jaw dysfunction RSI, carpal tunnel, ulnar neuritis, fibromyalgia, plantar fasciitis, tennis elbow, golfers elbow, reflex sympathetic dystrophy, CRPS (Chronic Regional Pain Syndrome), all tendonitis, joint stiffness, joint pain, muscle weakness, performance enhancement, constipation from neuropathic benefits from the spine and/or ingestion into gut and/or smooth muscle performance benefits, all spinal pain, sciatica, hip-spine syndrome, spinal mediated angina/vasomotor angina, chest disease, lung disease, asthma, palpitations, heartburn, reflux, costal chondritis, intercostal rib/muscle pain, hip pain, erectile dysfunction, prostate dysfunction, pancreatic dysfunction, deafness, visual effects/deficits, olfactory effects/deficits, adrenal dysfunction, sleep enhancement or sleep pattern normalization. It is also useful in the treatment of Depuytrens contractures, post-op scarring from actual surgery-direct dissolution/de-scarring effect, cosmetic facial wrinkles by local muscle relaxation/scar removal effect (topical, oral, direct inject, IV) or by neuropathic pain from spine (usually C1-C3).

As indicated, the present invention may be used to treat headache, including, but not limited to, tension headache, migraine headache, cluster migraine headache, headache from sinusitis, cervicogenic headache, TMJ headache and trigeminal neuralgia. The treatment may include a spinal component (e.g. paraspinal muscle), and/or a muscle (including myofascial) component (e.g. head (craniofascial) and neck muscles). For the spinal component, the selected fibrinolytic/proteolytic is injected paraspinally on one or both sides of the spine for the purpose of dissolving fibrin and/or scar tissue in paraspinal muscles to allow the vertebrae to relocate to the normal sitting position, to permit decompression of the discs, and/or decompression of the facet joint. The injection site will vary with the headache to be treated, and thus, may be injected paraspinally at the level of the neck (cervical spine), the thoracic spine or the lumbar spine. The treatment may include a single injection of fibrinolytic/proteolytic solution, or may include a dry preparatory injection to physically pierce or break up contracture at the treatment site. The site of injection will vary with the pathology being treated and the spinal segments involved. Paraspinal localization is conducted, as known by those of skill in the art, generally by palpating for the spinous process in the middle and then injecting paraspinally approximately 1-1.5 inches from midline. The depth of injection will vary with the condition to be treated, as well as the individual being treated (e.g. injection depth may vary with the size of the individual), for example, the injection depth may vary from about 5 mm to about 70 mm. The injection is generally done paraspinally straight down or with a slight angulation of about 10° towards the midline, although, this may vary from treatment to treatment. In many cases superficial injection of 5 mm may be enough to deliver the proteolytic treatment solution such that it will penetrate into the paraspinal muscles and dissolve the scar tissue leading to the spinal pathology. This could include the superficial muscles of the spine, the middle muscle groups such as the erector spinae, and the deep spinal muscles which may be called or referred to is the intrinsic spinal muscles and typically include the multifidus and the rotator brevis and rotator longus. Imaging, such as radiography, ultrasound or MRI, may be utilized to direct the injection, and to monitor progress of the treatment.

As indicated, the injection site will vary with the headache to be treated. Thus, for the treatment of tension headache, the proteolytic solution may be injected paraspinally between vertebral segments C4-6, and in more complex cases, may be injected at vertebral segments as high as C2 and as low as T2. For the muscle component of the treatment, the proteolytic solution may be injected into trapezius and/or sternocleidomastoid muscles. For treatment of migraine headache, the proteolytic solution may be injected between the skull and C1, and C1 and C2, and in more complex cases, may be injected in the thoracic spine from C2-7 and T1 down to T8. For the treatment of a cluster migraine, the proteolytic solution may be injected between the skull and C1, and C1 and C2, and in more complex cases, injected into the thoracic spine from T1 down to T8. For the muscle component of migraine (including cluster migraine) treatment, the proteolytic solution may be injected into the trapezius, sternocleidomastoid, temporalis, lateral ocular area of face, posterior occipital muscles, masseter, and medial pterygoids. The treatment of headache from sinusitis and for cervicogenic headache is similar to that for the treatment of migraine. The treatment for TMJ headache is also similar to migraine treatment, except for the muscle treatment component, proteolytic solution may be injected into the temporalis, lateral ocular area of face, masseter, and medial pterygoids. For trigeminal neuralgia, the treatment is similar to that of migraine, and may include additional muscle injection along the chin Perry central mental and sub mental areas. In each case, the proteolytic treatment solution is injected on the affected side, or on both sides, if required.

Paraspinal treatment may also be used for other pathologies as well. Treatments similar to those described above for headache may also be used to treat vertigo and/or tinnitus. For the treatment of bulging, herniated or degenerated disc, arthritis of the cervical, thoracic and/or lumbar spine, spinal cord compression and myelopathic pain and spinal stenosis, proteolytic solution may be injected paraspinally bilaterally at the affected vertebrae, and in more complex cases, above and below the affected vertebrae. For the muscle component of the treatment, superficial muscles of the spine such as the erector spinae and affected muscles nearby may also be injected. For the treatment of Carpal tunnel syndrome, proteolytic solution may be injected between C4-C7, and in more complex cases, may be injected as high as C2 and as low as T2. For the muscle treatment component, the pectorals, scalenes, sternocleidomastoids, and/or forearm flexor/pronator groups may also be injected. For treatment of Ulnar neuritis, proteolytic solution may be injected between C6-T1 (and as high as C2 and as low as T2, if required). Injection into the muscles, latissimus dorsi, teres groups, subscapularis, triceps, and/or medial flexors of forearm, may also be done. For the treatment of thoracic outlet syndrome, proteolytic solution may be injected between C4-T1 (and as high as C2 and as low as T2, if required), and may be injected into the pectorals, scalenes, sternocleidomastoids, forearm flexors/pronator groups, latissimus dorsi, teres groups, subscapularis, triceps, and/or medial flexors of forearm for muscle treatment. For tennis elbow or lateral epicondylitis, proteolytic solution may be injected between C5-C7 (and as high as C3 and as low as T1, if required), and may be injected into the forearm extensors/pronator groups. For golfers elbow or medial epicondylitis, proteolytic solution may be injected between C6-T1 (and as high as C2 and as low as T2, if required), and may be injected into the medial flexors of forearm. For rotator cuff injuries of the shoulder, proteolytic solution may be injected between C6-T4 (and as high as C2 and as low as T8, if required), and may be injected into the supraspinatus, infraspinatus, subscapularis and/or teres minor. For osteoarthritis of the shoulder, proteolytic solution may be injected between C6-T4 (and as high as C2 and as low as T8, if required), and may be injected into the supraspinatus, infraspinatus, subscapularis, teres minor, pectoral, latissimus dorsi, deltoids, trapezius, and/or rhomboids. For osteoarthritis of the elbow and plantar fasciitis, proteolytic solution may be injected between C4-T1 (and as high as C2 and as low as T8, if required), and may be injected into the forearm flexors, forearm extensors, triceps, and/or biceps. The spinal treatment is similar for osteoarthritis of the wrist bones, metacarpalphalangeal joints and phalangeal joints, and may include injection into the metacarpals, forearm flexors, forearm extensors, ulnar muscles, pectorals, and/or latissimus dorsi. For the treatment of osteoarthritis of the hips, proteolytic solution may be injected between T10-L1 and L4-S1 (and as high as T6 and as low as S2, if required), and may include injection into the iliopsoas, quadratus lumborum, iliotibial bands, hamstrings, adductors, quadriceps, and/or sartorius. For osteoarthritis of the knees, proteolytic solution may be injected between L1-L5 (and as high as T10 and as low as S2, if required), and may include injection into the adductors, hamstrings, quadriceps, iliotibial bands and/or gastrocnemius. For treatment of osteoarthritis of the ankles, proteolytic solution may be injected between L3-S1 (and as high as T10 and as low as S2, if required), and may include injection into the gastrocnemius, tibialis anterior, Petronius muscles, planters, and/or metatarsals. For treatment of osteoarthritis of the toes, proteolytic solution may be injected between L1-S1 (and as high as T10 and as low as S2, if required), and may include injection into the metatarsal, gastrocnemius and/or tibialis anterior. For treatment of osteoarthritis of the jaw, proteolytic solution may be injected between the skull and C1, and C1 and C2 (and in the thoracic spine from T1 to T8, if required), and may include injection into the temporalis, masseter, and/or medial pterygoids. For the treatment of Achilles tendonitis, proteolytic solution may be injected between L3-S1 (and as high as T10 and as low as S2, if required), into the gastrocnemius and/or plantaris in multiple sites typically along the line of the muscle. For Hamstring, Tibialis anterior tendinitis or Sciatica and piriformis syndrome, proteolytic solution may be injected between L4-S1 (and as high as T10 and as low as S2, if required), and may be injected between the hamstrings both immediately and laterally as needed, or the tibialis interior, typically along the line of the muscle, or into piriformis muscles and the medial lateral hamstrings. For the treatment of generally of tendinitis, proteolytic solution may be injected into the vertebrae that are associated with the immediate nerve supply of the target muscle group, and may be injected into the muscle component of the tendinitis. For the treatment of myelopathic and/or radicular pain of the spine and neuropathic pain, proteolytic solution may be injected at the vertebrae level where the suspected nerve compromise is located. In more complex cases the level above the level below will also be treated. And also in more complex cases the spinal have to be treated bilaterally. For scoliosis, proteolytic solution may be injected at the central location of the curvature to the ends of the curvature. Both sides of the spine will often require treatment.

The invention can also be used to cause or to allow organ remodeling and repair (heart, liver, lung, kidney, brain, pancreas, spleen, skin, bladder, prostate, breast) from the direct action of fibrinolytics/proteolytics, and/or to treat or mitigate the complications of diseases of these organs: in diabetes by improving pancreatic vascular disease thereby reversing pancreatic insufficiency/dysfunction or by remodeling or repairing the pancreas; in adrenal disease by improving adrenal vascular disease thereby reversing adrenal dysfunction or by remodeling or repairing the adrenal gland; in cardiac disease by improving cardiac vascular disease thereby reversing cardiac dysfunction or by remodeling or repairing the heart and/or vascular tissue; in Alzheimer's disease/dementia's by the dissolving of protein/fibrin deposits in brain tissue or by remodeling or repairing the brain, in spinal cord scarring by dissolving the fibrin/proteins deposited in or around the spinal cord.

The present invention is also thought to have anti-cancer effects, primarily as a result of the use of fibrinolytics, or secondarily, to have anti-neuropathic effects from treating spine/peripheral neuropathy. Neuropathy may initiate or promote neoplastic changes through chronic inflammation or tissue changes. The treatment or prevention or reversal of neuropathy that may lead to reduced risks of cancer or treat cancer are part of the invention. In addition, fibrinolytic/proteolytic activity may have direct anti-cancer effects related to reduced inflammation both regionally or globally within the body.

Other positive effects of the present method include visual benefits from macular degeneration and/or from visual accommodation in which the method aids in relaxing muscles affecting the lens of the eye, thereby preventing, treating presbyopia or other age-related eye diseases; and treatment of deafness, tinnitus and vertigo by reducing the scar formation within the bones/tissues of the auditory complex.

As stated above, the invention applies to all types of animals. Veterinarian applications for pain relief, and disease treatment or prevention are included within the scope of the invention. Feeding or applying the composition to farm animals, such as cows, pigs, chickens and lamb, may also be used to improve animal health, and to improve the quality of the meat yielded by treated animals (removal of scar tissue and deposits results in more tender meat product).

Other positive effects include sleep enhancement by reducing muscle tension (from fibrinlysis) allowing for normalization of sleep pattern. In addition, stroke and heart attack prevention and treatment, constipation prevention and treatment, and treatment of thyroid gland dysfunction, hypothyroid and hyperthyroid-(fibrinlysis in the gland and/or within its blood supply) are all benefits of the present method.

The invention may also be useful for the treatment of vocal cord scarring by dissolution of fibrin/proteins deposited in or around the vocal cord tissue and similarly for pulmonary fibrosis, COPD and/or asthma by dissolution of fibrin/proteins deposited in lung tissue.

The invention may also lead to improvement of taste from smell by dissolving fibrin and other proteins deposited in sinus and nasal tissue directly or indirectly by improved neurological function from dissolution of scar affecting the nervous system related to smell from spine or brain, and improve taste in theral taste buds by dissolving fibrin and other proteins deposited in and around the taste bud tissue directly or indirectly by improved neurological function from dissolution of scar affecting the nervous system related to taste from spine or brain, improvement in ability to swallow, dysphagia by dissolution of fibrin/proteins deposited in smooth muscle related to the motility of the pharynx and esophagus in swallowing or directly/indirectly by improved neurological function from dissolution of scar affecting the nervous system related to swallowing from spine or brain, or oral and esophagus tissue directly or by improvement of vascularity of the throat/esophagus thereby improving circulation to throat/esophagus and functionality of throat/esophagus.

Other advantages may include improvement in general gut motility by dissolution of fibrin/proteins deposited in smooth muscle for motility, or indirectly by improved neurological function from dissolution of scar affecting the nervous system related to gut motility from spine, brain, large or small intestine tissue, or sigmoid colon, or by improvement of vascularity of the gut thereby improving circulation to the gut and functionality of the gut; improvement in renal function by dissolution of fibrin/proteins deposited in smooth muscle of renal system, kidney tissue, ureter, bladder, urethra via motility, or directly/indirectly by improved neurological function from dissolution of scar affecting the nervous system related to the urological system (kidneys, ureters, bladder, urethra) from spine or brain, or kidney tissue directly, or by improvement of vascularity of the kidney thereby improving circulation to kidney and functionality of kidney; improvement in adrenal function by dissolution of fibrin/proteins deposited in smooth muscle of adrenal system, adrenal tissue via motility, or directly/indirectly by improved neurological function from dissolution of scar affecting the nervous system related to the adrenal gland and system from spine or brain, or adrenal tissue directly, or by improvement of vascularity of the adrenal gland thereby improving circulation to adrenal and functionality of adrenal gland; improvement in pancreatic function by dissolution of fibrin/proteins deposited in smooth muscle of pancreatic system, pancreatic tissue via motility, or directly/indirectly by improved neurological function from dissolution of scar affecting the nervous system related to the pancreas and pancreatic system from spine or brain, or pancreatic tissue directly, or by improvement of vascularity of the pancreas thereby improving circulation to pancreas and functionality of pancreas; improvement in liver and gallbladder function by dissolution of fibrin/proteins deposited in smooth muscle of the liver and gallbladder system, liver and gallbladder tissue via motility, or directly/indirectly by improved neurological function from dissolution of scar affecting the nervous system related to the liver and gallbladder from spine or brain, or liver and gallbladder tissue directly, or by improvement of vascularity of the liver and gallbladder thereby improving circulation to liver and gallbladder and functionality of liver and gallbladder; improvement in lung function by dissolution of fibrin/proteins deposited in smooth muscle of the lung, lung tissue via motility, or directly/indirectly by improved neurological function from dissolution of scar affecting the nervous system related to the pulmonary system from spine or brain, or lung tissue directly, or by improvement of vascularity of the lung thereby improving circulation to lungs and functionality of the lungs. Also included are improvements in cardiac function by dissolution of fibrin/proteins deposited in cardiac muscle of the heart, by improving conduction within the cardiac tissue by dissolving scar tissue that may contribute to various arrhythmias. There may also be benefits to the spine or cardiac tissue directly or by improvement of vascularity of the heart thereby improving circulation to the heart and functionality of the heart.

The invention also may be applicable to improvement in all brain function by dissolution of fibrin/proteins deposited in brain tissue, or by improving conduction within the brain tissue by dissolving scar tissue which may contribute to various seizures/abnormal brain activity including headache, behavioral, and cognitive effects. There may also be benefits to the spine that may improve brain function, brain disease, headache, facial pain, or brain tissue directly, or by improvement of vascularity of the brain thereby improving circulation to brain and functionality of the brain.

The invention may also lead to improvement in prostate function by dissolution of fibrin/proteins deposited in smooth muscle of prostatic system, or prostate tissue directly, or directly/indirectly by improved neurological function from dissolution of scar affecting the nervous system related to the prostatic system from spine or brain or by improvement of vascularity of the prostate thereby improving circulation to the prostate and functionality of prostate and also improvement in the ovary and fallopian tube function by the dissolution of fibrin/proteins deposited in the smooth muscle of ovary or fallopian tubes. The invention also may lead to improvement in ovarian, uterine, fallopian tube function by dissolution of fibrin/proteins deposited in smooth muscle of the female reproductive system or directly/indirectly by improved neurological function from dissolution of scar affecting the nervous system related to the female reproductive system from spine or brain. The invention may lead to improvement of vascularity of the ovary or fallopian tube thereby improving circulation to the ovary or fallopian tube and functionality of ovary and fallopian tube allowing for better fertility, general function, cycle function and/or delay in menopause.

In another aspect, the invention provides improvement in testicular function by the dissolution of fibrin/proteins deposited in smooth muscle of testicles, vasculature, and all spermatic transport tubular structures or directly/indirectly by improved neurological function from dissolution of scar affecting the nervous system related to the male reproductive system from spine or brain.

In a further aspect, there is provided direct/indirect benefits to the testicular/tubular tissue directly, or by improvement of vascularity of the testicular system thereby improving circulation to the testicles and functionality of testicles allowing for better fertility, function both hormonal and related to fertility.

EXAMPLES

Embodiments of the invention are described by reference to the following examples, which are not to be construed as limiting.

Example 1

A 50-year-old male suffered from chronic joint-pain for three years. The complaints are sore knees, sore hips, and sore low back. X-rays showed early changes of arthritis with sclerotic changes on x-rays in the knees and hips. Examination demonstrates scar formation, or trigger point formation detected in the muscles of the thighs and calves, swelling of the knees and tenderness in both hips with bursitis. He also has low back pain bilaterally involving much of the lumbar spine. MRI of the spine demonstrates compression of L1-S1 disks in vertebrae with multiple nerve roots compressed, likely contributing to neuropathic pain into his legs. The patient complained of numbness and tingling in both legs and feet and walks with great difficulty. The patient began oral fibrinolytic care starting with a low dose and gradually increasing to optimal dosing. Specifically, the patient was treated with 150,000 units Serrapeptase admixed with papain (1500 mg), bromelain (850 mg) and coq10 (100 mg) per day in 2-3 doses.

Over the course of three months, the patient noticed a decrease in swelling in both knees, decreasing pain of the low back, hips in the areas. His physician was able to demonstrate dissolution of scar detection or trigger point detection in the muscles of the thighs and calves and paraspinally. Over the course of two years, repeat MRI imaging demonstrated reversal of disk degeneration with increase in space between vertebrae. There was a reversal of nerve root entrapment within the lumbar spine at all sections. The patient had complete clearing of symptoms of numbness and tingling in the legs and feet, and his balance return to normal, and his gait and strength return to normal. The topical application of fibrinolytic care over the joints, specifically, the need joint, noted an accelerated benefit in the area. The injection of a liquid fibrinolytic/proteolytic into the deep spine where the intrinsic spinal muscles were located greatly accelerated the dissolution of the scar tissue in the muscles of the deep spine and this was measured on repeated spinal muscle biopsy.

Example 2

A 55-year-old female presented with weakness in both legs, ataxic gait, pain and numbness and burning of both legs and the pelvic area. Examination demonstrated pain and tenderness in the thoracic spine with retrolisthesis palpable at T5-T8. MRI examination demonstrates compressed discs from T5-T8. Between T5-T6 and T6-T7, two discs were herniated forwards onto the spinal cord touching the spinal cord. This was assigned as the major cause of the patient's lower body disability. The patient was biopsied paraspinally in the thoracic spine, and was found to have severe scarring in the upper back around the area of spinal pathology. She was injected with a fibrinolytic/proteolytic solution into the paraspinal muscles both superficially and deep going through all five layers of spinal musculature. The patient was treated with 6 injections (3 each side left and right) over T5-8 using a 2 inch needle (21 gauge). Each injection contained Urokinase (20,000 units) and Serrapeptase (20,000 units).

Scarring was felt through the biopsy at all levels. One week after the spinal injections, she had normalization of positioning of the thoracic vertebrae, 80% improvement in her lower body pain, near normalization of her walking ability, normalization of her ataxic gait to normal balance state, complete resolution of numbness and tingling in the lower body, and the re-biopsy of the thoracic spine demonstrated resolution of all scar tissue. MRI of the spine demonstrated correction of the retrolisthesis, great improvement in the spinal compression and decompression of the herniated discs off the spinal cord. The spinal stenosis seen on MRI had greatly improved. Over the course of 6 to 12 months, she continued to improve and made a full recovery.

Example 3

A 75-year-old Scottish male presented with right-handed Depuytrens contractures over the right fourth and fifth metacarpal palmar surface. The individual had curvature of the fourth and fifth digits due to the contractures in the palm of the hand. He was unable to straighten his fingers. He was treated with oral fibrinolytics (150,000 units Serrapeptase admixed with papain (1500 mg), bromelain (850 mg) and coq10 (100 mg) per day in 2-3 doses), and a topical lotion comprising 10,000 units of Serrapeptase mixed with dimethylsulfoxide (DMSO) that he applied three times a day to the palmar surface of his hand.

Over the course of three months, he had gradual improvement in range of motion of his hand in digits, and was able to return near full range of motion to his right hand digits and palm.

Example 4

A 35-year-old female had endometriosis and underwent open pelvic surgery with surgical removal of the endometriosis with ablation of endometrial lesions. This resulted in abdominal pain due to scarring from both the surgery and the disease itself. She suffered chronic abdominal pain with intermittent bowel symptoms. She was treated with both an oral fibrinolytic/proteolytic as described in Example 3, as well as by injection of fibrinolytic/proteolytic aqueous solution trans-abdominally through the umbilicus into her abdominal cavity once every two weeks. The solution contained 25,000 units of Serrapeptase solution.

The treatment resulted in gradual dissolution of scar tissue that had formed within the abdominal cavity around bowel, uterus, ovaries, kidneys and other abdominal structures. She noted gradual improvement over three months in her abdominal pain, abdominal tenderness, bowel function, and general well-being in her nominal and pelvic cavity.

Example 5

A 55-year-old female had wrinkles in the skin of her forehead, around the outer canthus of her eyes and had classical smoking lines around her mouth area. She was given the option of treatment by injection of fibrinolytic/proteolytic enzyme into the muscles of the face, such that the scar would be dissolved and the muscles would relax, or a topical cream as above to be applied to her facial area. She chose to use the cream around the area of her mouth and eyes. The cream included 10,000 units Serrapeptase and protease of proteolytics derived from serratia admixed with a standard cream. Subcutaneous injection using a 30G needle of a fibrinolytic aqueous solution including Serrapeptase (5000 units per site of injection) was performed at various sites on her forehead. She had great improvement and reduction in the appearance of the wrinkles in all areas.

Example 6

A 52-year-old man suffered from systemic lupus affecting the kidneys and brain. The scarring lesions were detected within the brain on MRI. It was suspected that these could be a risk for seizures or triggering seizures as he had one seizure. Furthermore, his kidney function had greatly reduced and MRI of the kidneys had demonstrated the appearance of scarring in the kidney structure. He had reduced kidney function as demonstrated on greatly elevated creatinine and urea. This was present for several years. He was treated with intravenous delivery of fibrinolytic/proteolytic enzymes to digest the proteinaceous scarring suspected in these two areas. He was treated with a weekly IV infusion of 200,000 units Urokinase for 4 weeks.

After one month, his serological testing demonstrated a normalization of his creatinine and urea function in the kidneys. MRI of the brain demonstrated reduction in scar formation seen on MRI. Treatment continued for total of six months. Over two years, the patient has not had any seizure activity since and his kidney function has maintained within normal ranges.

Example 7

A 45-year-old female who was slightly obese at 5'2" and 175 lbs. with a history of fibromyalgia developed non-insulin-dependent diabetes. She had 17 of 18 positive trigger-points (according to the ACR criteria of 1990 for fibromyalgia syndrome) three years ago. She was treated with oral diabetic medications. Her fasting blood sugars were elevated in the range of 10 to 15 (Canadian units normal is less than 6.0) and were not in the normal therapeutic range. MRA imaging of her pancreas suggested possible impaired arterial vascular supply to the pancreas itself. She was treated with oral fibrinolytic/proteolytic treatment as described in Example 3, which additionally included 100 mg of nattokinase per day, for six months.

Over the course of six months she had monthly serology, weighing in, an examination of are trigger points for fibromyalgia. Over the course of six months and monthly examinations, she had a progressive reduction in trigger point positivity for chronic pain in fibromyalgia, and progressive improvement in her blood sugars with 15 pounds of weight loss. Her fasting blood sugars normalized to the range of 4 to 6 in Canadian units. Her weight had dropped to 160 pounds. MRA imaging of the pancreas demonstrated what appeared to be normalization of arterial flow to the pancreas. The same treatment could be applied to patients with similar problems of the liver, spleen, kidneys, testicles, ovaries, with resultant improvement in function of the corresponding organs. We see improvement in liver function in individuals with a history of hepatitis and abnormal liver function. We see an improvement in creatinine and urea in people with a history of elevated creatinine levels. We see an improvement in both sperm production and quality in males with the history of infertility. In some females with a history of infertility, improvement is seen in ovulation through improved vascularity to the ovaries. While not wishing to be bound by a particular theory, the combination of improved vascular status and dissolution of deposited scar tissue appears to work in combination to aid in the improvement of these organs.

Example 8

A 35-year-old female presented with severe tension headaches intermittently 10 times per month on average. She requires over-the-counter anti-inflammatory or analgesic drugs, and occasionally a prescription opiate to control her headaches. She also reported some dental grinding and occasional jaw pain. Her examination demonstrated significant trigger point formation in the sternocleidomastoids, masseters and trapezius bilaterally. She also had reduced range of motion of her neck in all ranges but particularly rotation left and right. She was treated with injection of fibrinolytic solution (urokinase 2,000 to 20,000 units plus Serrapeptase 10,000 to 20,000 units injected at each site) to dissolve the trigger points over the trapezius, masseters and sternocleidomastoids which allowed for gradual dissolution of the trigger points in the area over the course of 48 hours allowing for improvement in jaw pain, less dental grinding, less jaw tightness, reduction in headaches, and better range of motion of her neck and rotation. A $2^{nd}$ set of similar injections 3 weeks later were performed to ensure longer-term recovery.

Example 9

A 44-year-old female suffering from recurrent migraine headaches, initiating from the right side posterior skull radiating over the right ocular area. She reported suffering migraines for 20 years which became more severe and more chronic over the past 2 years. She reported a constant daily headache, where the right side is always painful with intermittent aggravation of more profound right-sided headache that then goes global. She also reported extreme nausea, with vomiting at times. She reported significant jaw dysfunction bilaterally, but with more dysfunction on the right side. She reported occasional numbness and tingling in both hands, but particularly the right hand. Her examination demonstrated profound muscle pathology all along the cervical spine on the right and somewhat on the left and parts of her upper thoracic spine. She also had spasticity and trigger point formation of the trapezius, sternocleidomastoid, splenius groups, temporalis (tender to touch), as well as the occipital muscle, frontalis, and her sinus area (also tender to touch). She reported chronic sinus congestion. She was treated with injections of a fibrinolytic solution over the full cervical spine C1 to C7 bilaterally (solution was urokinase 2,000 to 20,000 units plus Serrapeptase 2,000 to 20,000 units). She was also treated by injection over the sternocleidomastoids, both at its insertion and along the muscle grouping, and along the trapezius bilaterally, as well as into her masseters and medial pterygoids, both injected bilaterally (solution as above with serrapeptase dosing adjusted to 10,000-20,000 units, using 1.5 inch 25 gauge needle). Additional injections into the temporalis, frontalis, and occipital muscle areas were done (solution as above adjusted to 2000 units serrapeptase per site at multiple sites using 1 inch 30 gauge needle). She also had some areas of her rotator cuff muscle groups injected including the supraspinatus and infraspinatus (solution as above with serrapeptase dosing adjusted to 5,000-10,000 units, using 1.5 inch 25 gauge needle). Over the course of a week she had progressive improvement of her headaches both chronic daily headache, migraine, sinus symptoms and jaw pain, as well as improved range of motion of her neck, shoulders, and jaw. She had improvement in shoulder strength and overall sleep comfort.

Example 10

A farmer with 100 head of adult cattle gave 50 head of cattle oral fibrinolytics mixed in with their feed for three months prior to slaughter. The oral fibrinolytics included daily 1,500,000 units of Serrapeptase, 3000 milligrams of nattokinase, 1,500,000 units of streptokinase and 8000 mg of bromelain. The other head of cattle were fed untreated cattle feed.

After slaughter, it was found that the treated cattle (with fibrinolytics) had softer, more tender meat that was more flavorful and perceived to be of a much higher grade of meat. Similar findings were found in the other parts of the cattle such as tongue, brain and the leather derived from the cattle was found to have less irregularities, was generally stronger, but of a softer hide of leather.

The invention claimed is:

1. A method to dissolve protein deposited in spinal, head or neck muscle to treat a secondary headache resulting therefrom in a patient in need thereof, said method comprising administering by injection into the spinal, head or neck muscle in the patient in need thereof, an effective amount of urokinase and an additional fibrinolytic agent selected from the group consisting of serrapeptase, nattokinase, and combinations thereof.

2. The method according to claim 1, wherein the urokinase and additional fibrinolytic agent are further administered in combination with at least one of a protease, an anti-inflammatory agent and an anti-oxidant.

3. The method of claim 2, wherein the urokinase and additional fibrinolytic agent are further administered with a serine protease.

4. The method according to claim 1, wherein the fibrinolytic agent comprises serrapeptase and nattokinase, and the urokinase and additional fibrinolytic agent are further administered with lipase, Rutin and amla.

5. The method according to claim 1, wherein the urokinase and additional fibrinolytic agent are further administered with one or more of papain, bromelain, coq10, and stretokinase.

6. The method according to claim 1, wherein the urokinase and additional fibrinolytic agent are further administered with pharmaceutically acceptable carrier.

7. The method of claim 1, wherein the urokinase and additional fibrinolytic agent are injected into a paraspinal muscle and one or more head or neck muscles.

8. The method of claim 1, wherein the urokinase and additional fibrinolytic agent are injected into at least one paraspinal muscle at the level of the cervical spine, the thoracic spine or the lumbar spine.

9. The method of claim 1, wherein the urokinase and additional fibrinolytic agent are injected into at least one muscle selected from the group consisting of the trapezius, sternocleidomastoid, temporalis, lateral ocular area of face, posterior occipital muscle, masseter, and medial pterygoid.

* * * * *